(12) United States Patent
Dhall

(10) Patent No.: US 10,485,697 B2
(45) Date of Patent: Nov. 26, 2019

(54) CEREBROSPINAL FLUID COOLING DEVICE

(71) Applicant: Sanjay Dhall, Mill Valley, CA (US)

(72) Inventor: Sanjay Dhall, Mill Valley, CA (US)

(73) Assignee: GREAT CIRCLE TECHNOLOGIES, INC., Mill Valley, CA (US)

( * ) Notice: Subject to any disclaimer, the term of this patent is extended or adjusted under 35 U.S.C. 154(b) by 300 days.

(21) Appl. No.: 14/257,135

(22) Filed: Apr. 21, 2014

(65) Prior Publication Data

US 2014/0316373 A1    Oct. 23, 2014

Related U.S. Application Data

(60) Provisional application No. 61/814,964, filed on Apr. 23, 2013.

(51) Int. Cl.
*A61F 7/12* (2006.01)
*A61M 1/00* (2006.01)

(52) U.S. Cl.
CPC .......... *A61F 7/12* (2013.01); *A61F 2007/126* (2013.01); *A61M 1/008* (2013.01)

(58) Field of Classification Search
CPC .............................. A61F 7/12; A61F 2007/126
See application file for complete search history.

(56) References Cited

U.S. PATENT DOCUMENTS

| | | | |
|---|---|---|---|
| 5,837,003 A * | 11/1998 | Ginsburg | A61F 7/12 606/27 |
| 6,146,411 A | 11/2000 | Noda | |
| 6,517,534 B1 * | 2/2003 | McGovern | A61B 18/1485 606/28 |
| 6,948,322 B1 | 9/2005 | Giblin | |
| 7,822,485 B2 * | 10/2010 | Collins | A61F 7/12 607/105 |
| 8,123,789 B2 | 2/2012 | Khanna | |
| 8,353,942 B2 | 1/2013 | Merrill | |

(Continued)

FOREIGN PATENT DOCUMENTS

| | | |
|---|---|---|
| JP | 2006-141993 | 6/2006 |
| JP | 2011-083315 | 4/2011 |
| WO | WO-2004/032720 | 4/2004 |

OTHER PUBLICATIONS

The Hypothermia After Cardiac Arrest Study Group, "Mild Therapeutic Hypothermia to Improve the Neurological Outcome after Cardiac Arrest," New England Journal of Medicine, 2002, 346(8):549-56.

(Continued)

*Primary Examiner* — Kaitlyn E Smith
(74) *Attorney, Agent, or Firm* — Morrison & Foerster LLP

(57) ABSTRACT

A device for topical cooling of the nervous system via cooling of cerebrospinal fluid, or CSF, using a solid thermally conductive material. The solid thermally conductive material is coupled to a heat exchange apparatus. The thermally conductive material may be coupled to any catheter that is used in existing clinical standard of care for acute neuronal injuries, such as catheters used to monitor and relieve intracranial pressure. The thermally conductive material is a biocompatible and solid material, for instance, metals such as steel, tungsten and titanium, and non-metallic materials such as thermal diamond paste.

12 Claims, 3 Drawing Sheets

(56) References Cited

U.S. PATENT DOCUMENTS

| | | | |
|---|---|---|---|
| 9,180,042 B2* | 11/2015 | Collins | A61F 7/12 |
| 9,358,138 B2 | 6/2016 | Kelley et al. | |
| 9,522,081 B2 | 12/2016 | D'ambrosio et al. | |
| 9,629,203 B1 | 4/2017 | Downs, Jr. | |
| 9,894,944 B2 | 2/2018 | Brooks et al. | |
| 9,981,137 B2 | 5/2018 | Eiger | |
| 10,085,879 B2 | 10/2018 | Pezzi | |
| 10,172,739 B2 | 1/2019 | Benyaminpour et al. | |
| 2002/0040717 A1 | 4/2002 | Dobak, III | |
| 2002/0198579 A1 | 12/2002 | Khanna | |
| 2004/0034399 A1 | 2/2004 | Ginsburg | |
| 2007/0005121 A1 | 1/2007 | Khanna | |
| 2007/0270926 A1 | 11/2007 | Serrano Molina | |
| 2008/0077088 A1* | 3/2008 | Collins | A61F 7/12 604/113 |
| 2008/0077206 A1* | 3/2008 | Collins | A61F 7/12 607/105 |
| 2010/0107657 A1 | 5/2010 | Vistakula | |
| 2010/0280438 A1 | 11/2010 | Thomas | |
| 2011/0029050 A1 | 2/2011 | Elefteriades | |
| 2012/0290052 A1 | 11/2012 | D'Ambrosio | |
| 2013/0025315 A1 | 1/2013 | Freeman et al. | |
| 2013/0197608 A1 | 8/2013 | Eiger | |
| 2014/0276715 A1* | 9/2014 | Shuman | A61B 18/082 606/28 |
| 2014/0303697 A1* | 10/2014 | Anderson | A61B 18/02 607/104 |
| 2014/0303698 A1 | 10/2014 | Benyaminpour et al. | |
| 2014/0316373 A1 | 10/2014 | Dhall | |
| 2015/0040300 A1 | 2/2015 | Murray et al. | |
| 2015/0173432 A1 | 6/2015 | Mccoy | |
| 2016/0022483 A1* | 1/2016 | Collins | A61F 7/12 607/105 |
| 2016/0317846 A1 | 11/2016 | Murray et al. | |
| 2016/0374411 A1 | 12/2016 | Brooks et al. | |
| 2017/0056240 A1 | 3/2017 | D'ambrosio et al. | |
| 2017/0145596 A1 | 5/2017 | Hays et al. | |
| 2017/0164675 A1 | 6/2017 | Buchert | |
| 2018/0103694 A1 | 4/2018 | Fortenbacher | |
| 2018/0264275 A1 | 9/2018 | Eiger | |
| 2018/0360652 A1 | 12/2018 | Ritrivi et al. | |
| 2019/0091063 A1 | 3/2019 | Benyaminpour et al. | |

OTHER PUBLICATIONS

Kammersgaard LP, et al., "Admission Body Temperature Predicts Long-Term Mortality After Acute Stroke: The Copenhagen Stroke Study," Stroke, 2002, 33(7):1759-62.

Krieger DW, et al., "Cooling for acute ischemic brain damage (COOL AID) An open pilot study of induced hypothermia in acute ischemic stroke," Stroke, 2001, 32(8):1847-54.

Schwab S, et al., "Moderate hypothermia in the treatment of patients with severe middle cerebral artery infarction," Stroke, 1998, 29(12):2461-66.

Polderman KH, "Application of therapeutic hypothermia in the intensive care unit," Intensive Care Medicine, 2004, 30(5):757-69.

Saunders N, et al., "Barrier Mechanisms in the Brain, I. Adult Brain," Clinical and Experimental Pharmacology and Physiology, 1999, 26(1):11-19.

Shannon CN, et al., "The economic impact of ventriculoperitoneal shunt failure," Journal of Neurosurgery Pediatrics, 2011, 8:(6):593.

Mori MD, et al., "An Epidural Cooling Catheter Protects the Spinal Cord Against Ischemic Injury in Pigs," The Annals of Thoracic Surgery, 2005, 80(5):1829-33.

Moomiae RM, et al., "Novel Intracranial Brain Cooling Catheter to Mitigate Brain Injuries," J NeuroIntervent Surg, 2012, 4:130-133.

Polderman and Callaghan, "Equipment review: Cooling catheters to induce therapeutic hypothermia," Critical Care, 2006, 10:234.

Chesnut RM, et al., "A trial of intracranial-pressure monitoring in traumatic brain injury," New England Journal of Medicine, 2012, 367(26):2471-81.

Sosin, et al., "Incidence of mild and moderate brain injury in the United States, 1991" Brain Injury, 1996, 10(1):46-54.

Taccone F, "When, where and how to initiate hypothermia after adult cardiac arrest," Minerva Anestesiol, 2011, 77: 927-33.

Diringer MN, "Treatment of fever in the neurologic intensive care unit with a catheter-based heat exchange system," Critical Care Medicine, 2004, 32(2):559-64.

Haugk M, et al., "Feasibility and efficacy of a new non-invasive surface cooling device in post-resuscitation intensive care medicine," Resuscitation, 2007, 75(1):76-81.

Flemming K, et al., "Comparison of external and intravascular cooling to induce hypothermia in patients after CPR," GMS German Medical Science, 2006, 4:Doc4.

Wong GK, et al., "External Ventricular Drain Infection," Journal of Neurosurgery, 2007, 107(1):248.

MEDEXSUPPLY, "Cincinnati Sub-Zero Blanketrol III Hyper-Hypothermia System," 2013, Available at: (https://www.medexsupply.com/orthopedic-therapy-hot-cold-therapy-heating-units-gel-warmers-cincinnati-sub-zero-blanketrol-iii-hyper-hypothermia-system-x_pid-32065.html?products_id=32065).

Rutland-Brown W, et al., "Incidence of traumatic brain injury in the United States," The Journal of Head Trauma Rehabilitation, 2006, 21(6):544.

Edsbagge M, "Spinal CSF absorption in healthy individuals," American Journal of Physiology: Regulatory, Integrative & Comparative Physiology, 2004, 56(6):R1450-R5.

Yoshida K, et al., "Phase-contrast MR Studies of CSF Flow Rate in the Cerebral Aqueduct and Cervical Subarachnoid Space with Correlation-based Segmentation," Magnetic Resonance in Medical Sciences, 2009, 8(3):91-100.

Bondy GP, "Pathology 425 Cerebrospinal Fluid (CSF)," Department of Pathology and Laboratory Medicine at the University of British Columbia, 2011.

CDC Centers for Disease Control and Prevention, "Spinal Cord Injury (SCI): Fact Sheet," Available at http://www.cdc.gov/traumaticbraininsury/scifacts.html visited on Apr. 23, 2014. 4 pages.

Harris, et al., (2009) "Discrete Cerebral Hypothermia in the Management of Traumatic Brain Injury: A Randomized Controlled Trial," Journal of Neurosurgery, 110(6): 1256-1264.

Office Action dated Apr. 3, 2018, directed to JP Application No. JP-2016-510719; 6 pages (Machine translation).

Penguin Cold Caps, "Cap Information," Available at http://penguincoldcaps.co.nz/public/default.php?page=17 visited on Apr. 28, 2014. 2 pages.

Vidal CN, et al., (2008) "Three-dimensional mapping of the lateral ventricles in autism," Psychiatry Research: Neuroimaging, 163:106-115.

International Search Report and Written Opinion dated Sep. 19, 2014 directed International Application No. PCT/US2014/034798.

First Office Action dated Oct. 20, 2017, directed to CN Application No. 201480034015.8; 8 pages.

Extended Search Report dated Nov. 11, 2016, directed to EP Application No. 14789033.9; 8pages.

Examination Report No. 1 dated Jan. 22, 2018, directed to AU Application No. 2014257323; 5 pages.

Dhall., U.S. Office Action dated Apr. 12, 2019, directed to U.S. Appl. No. 15/369,391; 31 pages.

Notice of Reasons for Refusal dated Feb. 26, 2019, directed to JP Application No. JP-2016-510719; 6 pages.

Second Office Action dated Aug. 24, 2018, directed to CN Application No. 201480034015.8; 5 pages. (with English translation).

* cited by examiner

CEREBROSPINAL FLUID COOLING DEVICE

CROSS REFERENCE TO RELATED APPLICATION

This application claims the benefit of priority of U.S. Provisional Application 61/814,964.

BACKGROUND OF THE INVENTION

1. Field of the Invention

The present invention relates to devices for inducing hypothermia

2. Description of the Related Art

Strokes, Traumatic Brain injury, and Spinal Injury commonly pose significant risk of permanent damage to the spinal cord and brain. Similarly, multiple diseases/events/procedures including but not limited to heart disease, cardiac arrest, and major surgery may be followed by cerebral and spinal cord ischemia, which in turn can lead to permanent neurologic damage. Recovery from severe brain injury resulting from ischemia, stroke, hemorrhage, or trauma is uncommon. The permanence and untreatable nature of neurologic injury requires speedy mitigating treatment and care.

It has long been believed that hypothermia may mitigate brain damage. Treatment by mild hypothermia after cardiac arrest was initially reported in the late 1950s and early 1960s. The Hypothermia after Cardiac Arrest Study Group, "Mild Therapeutic Hypothermia to Improve the Neurologic Outcome after Cardiac Arrest." New England Journal of Medicine 346.8 (2002): 549-56. The reason for its benefits have not been proven, but induction of mild hypothermia has been hypothesized to significantly decrease intracranial pressure and secondary neurological injury in various types of brain injury, including traumatic brain injury, ischemic stroke, intracranial hemorrhage, and hepatic encephalopathy. Thus, hypothermia continues to be a hopeful tool to prevent, protect against, or mitigate neurologic injury.

In tact, induction of systemic hypothermia, i.e. hypothermia induced to the whole body, is an accepted initial step in the management of patients who survive cardiac arrest. Devices for inducing systemic hypothermia include cooling pads and vascular catheters. Systemic hypothermia is associated, however, with a host of negative side effects including bleeding diathesis, shivering, arrhythmias, suppression of the immune system resulting in increased susceptibility to infection, and electrolyte imbalance.

Thus, there is growing, interest in techniques that would provide neuroprotective benefits without the harmful side effects of systemic hypothermia. Currently known devices for selective cooling of the nervous system include cooling helmets and catheters that circulate cooled saline, but have been of limited efficacy due to failure to consistently dissipate heat or adverse side effects. Furthermore, methods using circulating liquids are limited by the freezing point of the liquid, and risk rupture and contamination.

BRIEF SUMMARY OF THE INVENTION

It is an object of the present invention to selectively cool the nervous system and prevent neuronal injury, and to use a material with thermally conductive properties that has greater cooling efficacy and less risk of damage to the human body. The present invention is a device for topical cooling of the nervous system via cooling of cerebrospinal fluid, or CSF. CSF functions as a cushion for and circulates around the brain and spinal cord. The present invention uses a solid thermally conductive material, coupled to a heat exchange apparatus, to cool surrounding CSF. The thermally conductive material may be coupled to any catheter that is used in existing clinical standard of care for acute neuronal injuries, such as catheters used to monitor and relieve intracranial pressure. The thermally conductive material is a biocompatible and solid material, for instance, metals such as steel, tungsten and titanium, and non-metallic materials such as thermal diamond paste.

BRIEF DESCRIPTION OF THE DRAWINGS

In the following drawings, like reference numbers have been used wherever possible to indicate like parts in different views.

DETAILED DESCRIPTION OF THE INVENTION

Figure 1:
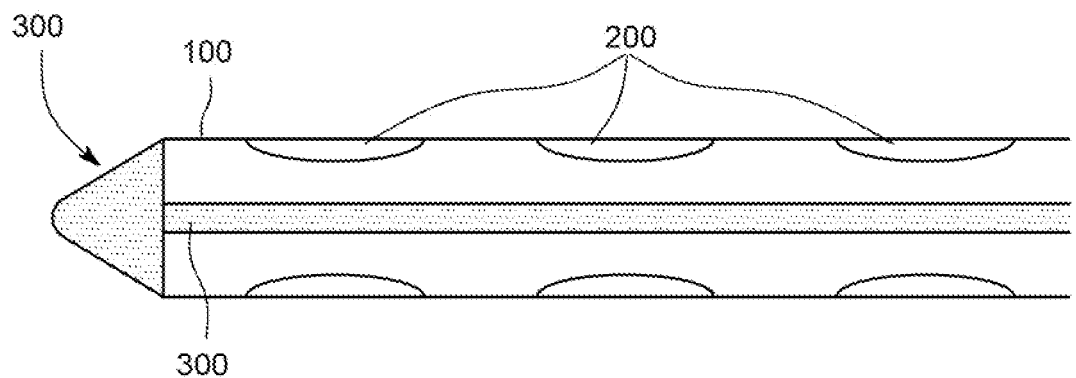
FIG. 1 shows a device of the present invention.
Figure 3:
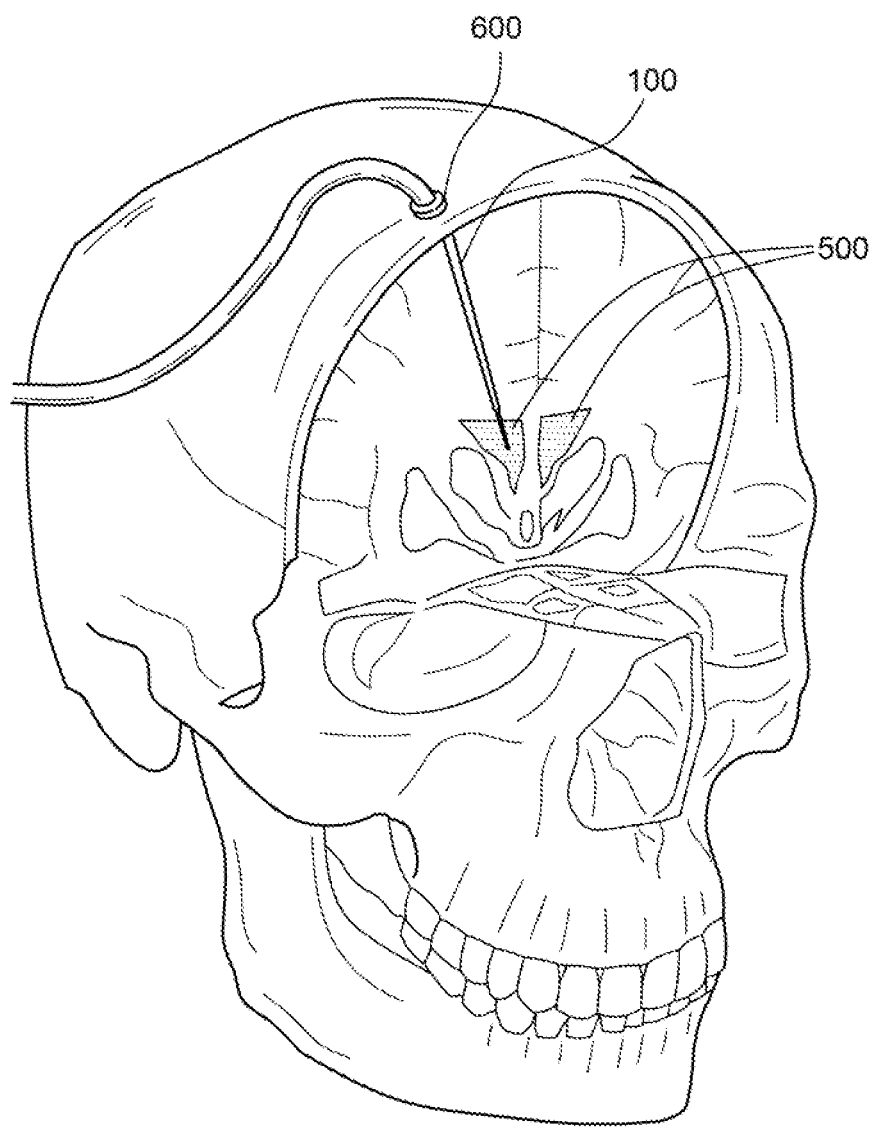
FIG. 3 shows insertion of the catheter into the lateral ventricle of the brain.

With reference to FIG. 1, the preferred embodiment of the present invention comprises a drainage catheter 100, which is commonly used to regulate pressure within the brain during treatment for brain and spinal cord injuries. The drainage catheter 100 is typically inserted into lateral ventrical 500 of the brain, as depicted in FIG. 3, and may comprise any combination of known monitoring sensors, such as pressure transducer, oxygen monitor, and temperature gauge. As pressure builds, CSF enters catheter 100 through openings 200 and flows out of the skull.

The present invention comprises a solid thermally conductive material 300 that is operable to reduce CSF temperature. The thermally conductive material is biocompatible, i.e. a material that elicits minimal response from the body. Thermally conductive and biocompatible materials including metals such as tungsten and titanium, and carbon-based materials such as thermal diamond paste or diamond coating, are contemplated. Preferably, the thermally conductive material does not cause thermomagnetic effects that may disrupt procedures such as MRI.

The thermally conductive material is coupled to a heat exchange apparatus operable to adjust the temperature of the material. Heat exchangers are known in the art and may include any fluid, gas, electric, or other heat exchangers. In a preferred embodiment, the heat exchanger is attached to a standard wall outlet.

Figure 2:
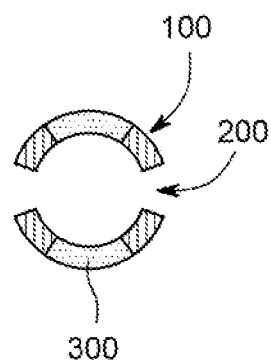
FIG. 2 shows a cross-section of the catheter of the present invention.

The thermally conductive material 300 is situated on the catheter to optimize temperature distribution, such as by maximizing surface area. In a preferred embodiment as depicted in FIG. 1, the thermally conductive material 300 is located on the tip of the catheter, and also in embedded strips on the outer surface of the catheter. Cross-section FIG. 2 shows how embedded strips 300 are distributed over the outer surface of the catheter, in between drainage openings 200. While it is desirable to place the thermally conductive material so that the catheter remains flexible, it will be evident to those skilled in the art that inflexible catheters may also be placed into the brain.

Figure 4:
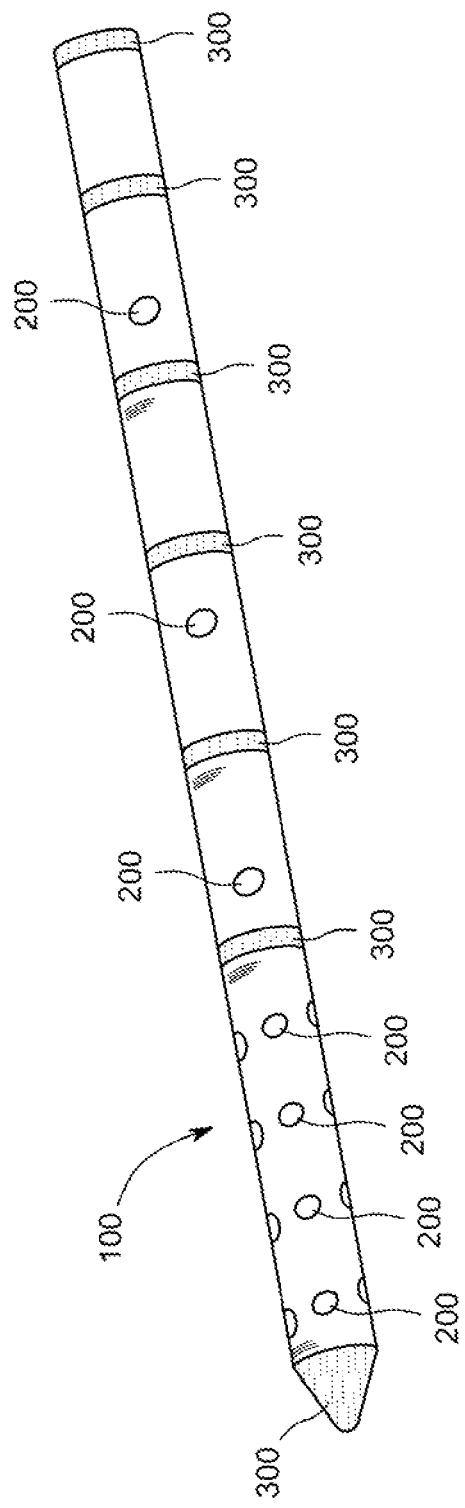
FIG. 4 shows an alternatively configured device of the present invention.

In an alternative embodiment, depicted in FIG. 4, the invention comprises a thin metal frame made from thermally conductive material 300. The thermally conductive frame may be disposably or reusably attachable to a standard drainage catheter, sterilizable through stringent chemical or autoclave sterilization techniques. The thermally conductive frame is attachable around the outside of the catheter 100, with thermally conductive cap at the distal end. The thermally conductive frame is flexible so that it may be used when tunneling through the skull and through the brain.

Many configurations of catheter and thermally conductive material are possible without departing from the spirit of the invention. For instance, the device may comprise a thermally conductive element that is hollow and insertable into a standard drainage catheter, wherein the insertable thermally conductive element comprises a perforated tip through which ventricular drainage occurs. Once intracranial and atmospheric pressure have been equalized, no net flow of CSF would occur and the thermally conductive element would cool CSF as it circulates the brain and spinal cord.

In another embodiment, the device may comprise a catheter with a perforated and thermally conductive tip for simultaneous cooling and draining, wherein wires on the inside of the catheter are lined with a thermally conductive material. In yet another embodiment, the tip of the catheter comprises a sphere of thermally conductive mesh material to allow for simultaneous draining and cooling, wherein the thermally conductive mesh is operable to open and close to maximize or minimize the surface area for cooling.

As will be evident to one of ordinary skill, the cooling catheter is complimentary to, compatible with, or may replace existing and standard lateral ventricle drainage procedures to relieve intracranial pressure. While insertion into the ventricle is the standard of care to relieve intracranial pressure, the purpose of the present invention is to cool CSF and as such the catheter may be placed anywhere in the body that CSF is found.

In the preferred embodiment, the catheter also comprises a temperature sensor to measure the temperature of surrounding tissue. When used in the brain the temperature sensor is preferably located near the proximal end of the catheter, so that it can measure the temperature of brain tissue. In the preferred embodiment, the catheter further comprises an intracranial pressure monitor 600, used during standard procedures to prevent neuronal injury.

As many possible embodiments may be made of the invention without departing from the scope thereof, and it is to be understood that all matter set forth herein or shown in the accompanying drawings is to be interpreted as illustrative and not in a limiting sense.

What is claimed is:

1. A device configured to be inserted into cerebrospinal fluid of a patient, the device comprising:
    a catheter body comprising drainage openings; and
    a solid thermally conductive material that is different than a material of the catheter body and is located on a tip of the catheter body and embedded in the catheter body in at least two strips that extend longitudinally along opposite sides of the catheter body from the tip and between the drainage openings of the catheter body and radially from an outer surface of the catheter body to an inner surface of the catheter body;
    wherein the solid thermally conductive material is thermally coupled to a heat exchange apparatus, and wherein the heat exchange apparatus is operable to transfer heat to and from the solid thermally conductive material by solid conduction.

2. The device of claim 1, wherein the device is configured to monitor intracranial pressure.

3. The device of claim 1, wherein the device is configured to drain cerebrospinal fluid.

4. The device of claim 1, wherein the device is a catheter for intracranial drainage.

5. The device of claim 1, wherein the solid thermally conductive material is metal.

6. The device of claim 1, wherein the solid thermally conductive material is non-metallic.

7. A method comprising:
    inserting a device into cerebrospinal fluid of a patient, wherein the device comprises:
        a catheter body comprising drainage openings;
        a solid thermally conductive material that is different than a material of the catheter body and is located on a tip of the catheter body and embedded in the catheter in at least two strips that extend longitudinally along opposite sides of the catheter body from the tip and between the drainage openings of the catheter body and radially from an outer surface of the catheter body to an inner surface of the catheter body;
        wherein the solid thermally conductive material is thermally coupled to a heat exchange apparatus located outside of the body; and
    operating the heat exchange apparatus to cool the thermally conductive material by solid conduction.

8. The method of claim 7, wherein the device is operable to monitor intracranial pressure.

9. The method of claim 7, wherein the device is operable to drain cerebrospinal fluid.

10. The method of claim 7, wherein the device is a catheter for intracranial drainage.

11. The method of claim 7, wherein the solid thermally conductive material is metal.

12. The method of claim 7, wherein the solid thermally conductive material is carbon-based.

* * * * *